United States Patent [19]

Ueberle et al.

[11] Patent Number: 4,819,621
[45] Date of Patent: Apr. 11, 1989

[54] METHOD FOR DETECTION OF CAVITATIONS DURING MEDICAL APPLICATION OF HIGH SONIC ENERGY

[75] Inventors: Friedrich Ueberle, Dossenheim; Rainer Riedlinger, Karlsruhe, both of Fed. Rep. of Germany

[73] Assignee: Richard Wolf GmbH, Knittlingen, Fed. Rep. of Germany

[21] Appl. No.: 17,752

[22] Filed: Feb. 24, 1987

[30] Foreign Application Priority Data

Mar. 11, 1986 [DE] Fed. Rep. of Germany ....... 3607949

[51] Int. Cl.⁴ ........................ A61H 1/00; A61B 17/22; A61B 10/00
[52] U.S. Cl. ................................. 128/24 A; 128/328; 128/660.01
[58] Field of Search ............. 128/660, 328, 305, 24 A, 128/662; 73/599, 602

[56] References Cited

U.S. PATENT DOCUMENTS

| | | | |
|---|---|---|---|
| 3,934,458 | 1/1976 | Beretsky et al. | 73/602 |
| 4,338,948 | 7/1982 | Perez-Mendez et al. | 73/602 X |
| 4,395,909 | 8/1983 | Steinberg et al. | 128/660 X |
| 4,412,544 | 11/1983 | Beretsky et al. | 73/620 X |
| 4,513,750 | 4/1985 | Heyman et al. | 128/660 |
| 4,539,989 | 9/1985 | Forssmann et al. | 128/328 |
| 4,586,512 | 5/1986 | Do-huu et al. | 128/660 |
| 4,614,178 | 9/1986 | Harlt et al. | 128/24 A |
| 4,617,931 | 10/1986 | Dory | 128/328 |
| 4,662,380 | 5/1987 | Riley | 128/660 |
| 4,689,986 | 9/1987 | Carson et al. | 128/660 X |

OTHER PUBLICATIONS

Sauerbruch, T. et al., "Fragmentation of Gallstones by ESW", NEJM Mar. 27, 1986, pp. 818–822.
Wells, P. N. T., "Ultrasonic Diagnosis", Academic Press, N.Y. 1977, pp. 430–435.

Primary Examiner—Francis J. Jaworski
Attorney, Agent, or Firm—Willian Brinks Olds Hofer Gilson & Lione Ltd.

[57] ABSTRACT

A method and apparatus are described for the detection of possible tissue injuries caused by cavitation during the medical application to a patient's body of high sonic energy which is generated extraneously by means of a sonic transducer for destruction of an element—for example a concretion—which is present in a target area. To detect the possible occurrence of cavitation the target area is acted upon by an acoustic test signal and a reception signal is generated from at least an initial reflection of the test signal. This signal is then examined by comparison with the test signal to detect the presence of an impedance jump leading to an attenuated reflection, so that a control signal may be generated upon detection of an impedance jump of this nature. Audible or visible warning signals may be engendered among others, and the sonic transducer may be deactivated if need be, by means of this control signal.

18 Claims, 1 Drawing Sheet

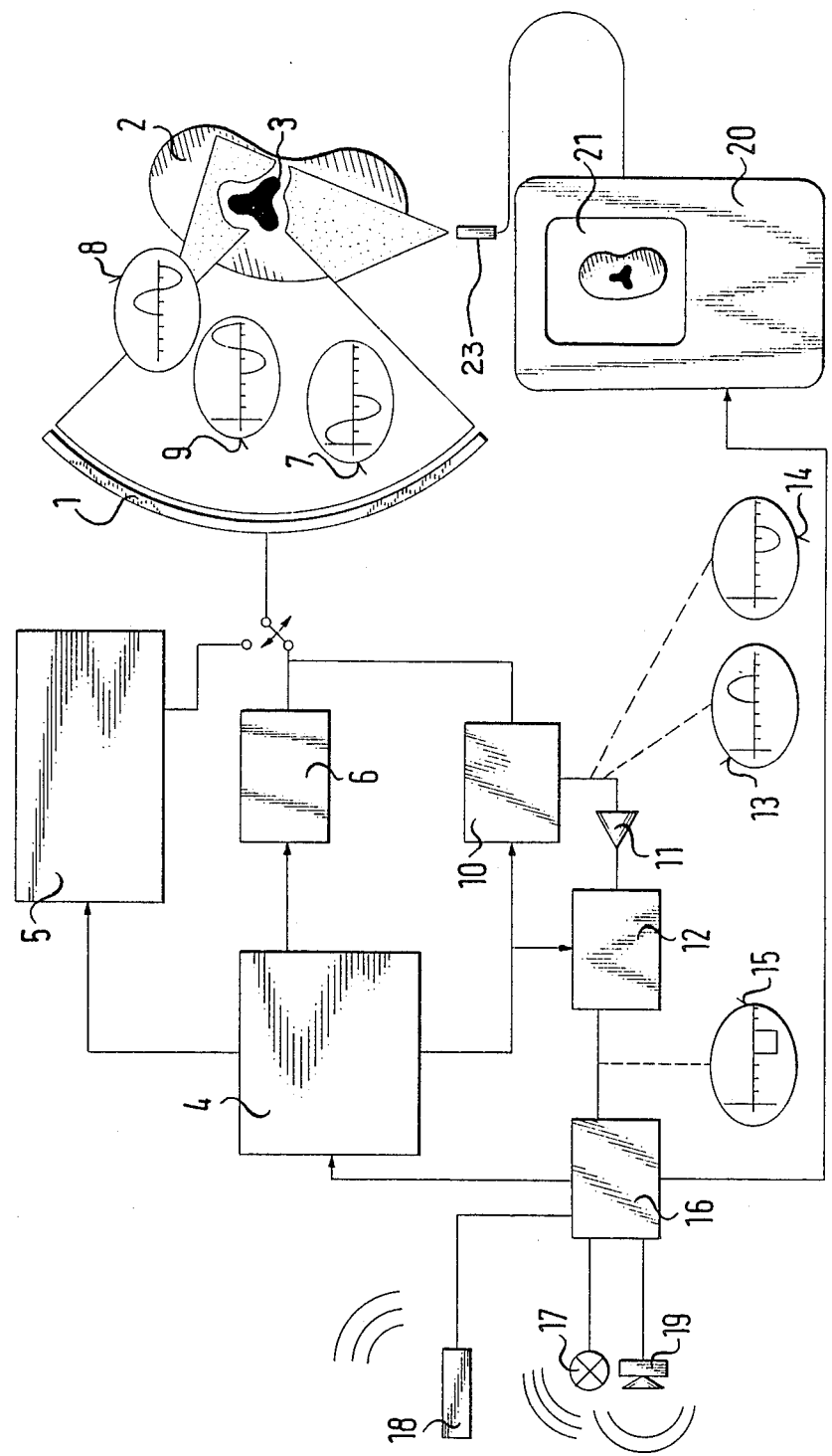

4,819,621

METHOD FOR DETECTION OF CAVITATIONS DURING MEDICAL APPLICATION OF HIGH SONIC ENERGY

BACKGROUND OF THE INVENTION

1. Field of the Invention

The invention relates to a method for detection of possible tissue injuries based on cavitational actions during the medical application of high sonic energy, which is generated extraneously by a sonic transducer and transmitted on to and into the patient's body via coupling means, the sonic field traversing a spatial section internal to the body and being focused on a target area or zone, to destroy a section present within the target area, for example concretion or a tissue section.

2. Description of the Prior Art

Upon exposing a human body to ultrasonic or shock waves for the purpose of destroying concretions, there is a risk of damaging the tissue for a variety of reasons. These include thermal injuries on the one hand, which may be prevented comparatively easily by adjusting the sonic dosage, and on the other hand damage caused by cavitational actions which are commonly difficult to predict and avert, since it is not always known precisely whether and when cavitational actions should be expected within the area exposed to sonic action.

Furthermore, it is very difficult when generating powerful sonic pressures, such as are required for example to break up stone concretions within a kidney, the gall-bladder or the bladder, to generate purely positive sonic pressures only. As a matter of fact, substantial negative pressures frequently also arise, leading to cavitational actions, in which the body fluid is practically disintegrated and gas bubbles are generated which may cause tissue cells to explode.

There are other fields moreover for the medical application of high-power ultrasonics, that is to say in the case of cancer treatment for example, in which cavitational actions are required however to destroy tissue cells and "tissue damage" is thus engendered deliberately by cavitational actions. In such cases too the detection of cavitational actions is of importance particularly since the destruction of unaffected tissues should be prevented and since it is of importance for the physician in charge to know whether and when the cavitational actions occur in the patient's body.

SUMMARY OF THE INVENTION

It is an object of the invention to provide a method which allows early detection of cavitational actions which might give rise to injury and thereby creates a situation in which the physician in charge may intervene opportunely and by appropriate measures prevent grave injury to the patient.

This object is achieved in accordance with the invention in that for example during the exposure of the body to high sonic energy, or during brief intervals between separate exposures to sound, the target area is acted upon by an acoustic test signal, a reception signal is formed from at least one reflection of the test signal said reception signal is checked by comparison to the test signal to discover whether a marked changed in impedance (referred to herein as an "impedance jump") is present causing a weak sonic reflection, and a control signal is generated upon detecting an impedance jump of this nature.

According to the invention, use is thus made of the fact that a sound-absorbent reflector rotates the phase of a sonic signal incident from a less absorbent medium through 180°, so that positive pressure surges are reflected as negative pressure surges, and vice versa. It is thus possible to deduce from a change of polarity of the sonic signal, that the signal must have struck a sound-absorbent reflector and that an impedance jump will be present thereat, for example between tissue or fluid and gas.

Knowing the polarity of the test signal, it is now possible to detect without ambiguity by comparison of this polarity with the polarity of the reflected signal, whether an unattenuated reflection is present in view of identical polarities or whether an attenuated sound reflection is present in view of dissimilar polarities. Since reflectors which are sound-absorbent compared to water are not normally found in the body, excepting gases in the lungs or intestinal tract, the detection !of such attenuated reflections is a comparatively certain indication of the occurrence of cavitational actions and a motivation for generating the control signal which may be evaluated in a variety of ways, for example as a warning signal.

The nature of the reflection may be detected in the simplest case by oscilligraphic display and observation of the signals in question. Since it is preferable however to have an automatic detection and analysis, inclusive of generating a control or alarm signal, the reception signal may for example be observed within a time slot, by storing a half-cycle of the reception signal within a memory or hold circuit and comparing the same to the co-ordinated half-cycle of the test signal in respect of polarity, so that the control signal may be generated upon detecting different polarities. In this connection, if the initial half-cycle of the test and reception signals are analysed and the first half-cycle of the test signal always has positive polarity, the hold circuit should consequently be able to react only to negative reception signals in principle, without the need to scan for the specified polarity of the test signal and for an immediate comparison in each case between the polarities of both half-waves.

Other aids may be applied as well for the purpose of signal analysis, instead of the aforesaid time slot. In this connection, it is possible to contemplate an amplitude gap as well as other data processing methods, say such as conversion, correlation, cepstrum and the like or a combination of such methods known per se.

To capture and evaluate an impedance jump caused by a cavitational action, it is also possible moreover to have recourse to the detailed structure of the reflection or reflections, such as the amplitude of the individual reflected half-waves and/or amplitude sequence of several such half-waves and to plot these for evaluation in correlation or comparison with the amplitude and/or amplitude sequence of the test signal.

The possibility exists furthermore of exploiting not only the initial reflection or echo of the test signal as a reception signal, but also one or more multiple echoes between the target area or target object and the test pulse transmitter or an appropriate auxiliary reflector, the graph shapes of the echoes in question then being considered and interpreted appropriately for evaluation purposes.

Finally, it is not absolutely necessary to perform the momentary evaluating actions under application of actual electronic circuitry, since the actions and measures in question may also be formulated as an algorithm of a computer program. In this connection, it is also possible to encompass and evaluate an enlarged zone by scanning a longer period of the reception signal and seeking a signal which corresponds to a signal occurring in the case of an attenuated echo, in the computer by establishing the cross-correlative function between the actual reception signal and a reference signal.

A logical application of the inventive method may be considered notwithstanding the wide range of possibilities listed for detection and interpretation of the impedance jumps of interest for this purpose, in particular in conjunction with an existing system for location and disintegration of stone concretions. Known systems of this nature are illustrated and described, for example in the German OS text Nos. 2722252, 3122056 and 3220751. In essence, they comprise a high-power sonic transmitter and a locator system comprising at least one monitor whereby the focus of the sonic transducer may be aligned under observation on the concretion lying in the target area.

As already stated, this sonic transmitter may be utilised to generate the test signals on the one hand, and on the other hand also for reception of the echo or reflection signals.

On the other hand, the possibility evidently also exists that a separate transmitter may be provided for the test pulses and a separate receiver may be provided for reception of the echo signals, in which connection the transmitter and receiver should then be coupled mechanically with the high-power sonic transducer and the location system so that a geometrically unequivocal association and correlation between the target zones of both the transmitting and receiving systems are always assured.

It is possible moreover that a monitor of the location system which is available in any case may be utilised for the optical display of the warning signal derived from the control signal, in which connection a warning colouration, warning symbols or the like may for example appear on the image screen of the monitor. On the other hand, the warning signal may also be offered to the user as an audible or other perceptible signal.

Notwithstanding whether the high-power sonic transmitter is or is not co-opted to generate the test signals, it should be deactivated automatically at the first or repeated appearance of warning signals, or be operable under reduced power at least, to prevent tissue damage caused by intervening cavitational actions and to provide the user with the possibility of initial examination of the situation and of reaching a decision on whether the high-power sonic transducer may be placed in operation again or whether a renewed location of the concretion and a more precise alignment of the transducer focus on the concretion are needed. The same evidently and logically also applies in the case of locating tissue sections which should be destroyed and of the alignment of the focus on such tissue section.

BRIEF DESCRIPTION OF THE DRAWINGS

The accompanying drawing illustrates in a diagrammatic and simplified manner, as a block diagram, a preferred embodiment of the invention.

DETAILED DESCRIPTION OF THE PREFERRED EMBODIMENT

The high-power sonic transducer 1 which is intended to operate as a transmitter and receiver in this case, may be aligned in known manner and under observation with its focus, for example on a concretion 3 present in the kidney 2. The generator 5 is energised at a particular present repetition rate by means of a control stage 4, so that this generator may supply the transducer 1 with current pulses at that repetition rate for the purpose of generating sound pulses of high power, which are transmitted via a coupling means not shown in particular, such as water, on to and into the patient's body.

When test pulses are to be generated for detection of cavitational actions, the test pulse generator 6 is activated by the control stage 4, whereas the generator 5 is deactivated, so that the transducer 1, now supplied with current pulses via the generator 6, transmits acoustic test pulses 7 into the target zone. This results in signals 8,9 reflected with or without, attenuation A test signal 9 reflected with attenuation and having a polarity altered as compared to the actual test signal 7 leading to the conclusion that the focus of the transducer 1 is situated on or within a gas bubble.

The reflected sonic signals are converted into electrical reception signals and conducted to a reception gate 10 which is controlled by the control stage 4 in conjunction with the time slot described in the foregoing so that, for example, it is unblocked in each case at the appearance of the initial half-wave of the reception signals and allows this half-wave to pass to a selective hold circuit 12 via a signal amplifier 11. A half-wave 13 of this nature—in the case of an unattenuated reflection and another half-wave 14—in the case of an attenuated reflection, are shown in the illustration.

As had already been stated above, the hold circuit 12 may react in this particular case to negative leading half-waves 14 only on the reception signal, if the initial half-wave of the test signal 7 is always positive, since it is then this situation only which is of significance for detection of cavitational actions. The signal 15 thus stored in a hold circuit 12 is received by a comparator circuit 16, which detects the signal polarity and—in the specified case, that is to say in the presence of a signal 15 indicating an attenuated reflection generates a control signal which may be utilised as a warning signal, for example to active an optical signal transmitter 17 or optional acoustic signal transmitter 19, or other perceptible signal transmitter 18.

Alternately or complementarily, the comparator 16 may also transmit a control signal to the control circuit 4 which may then, for example, block the pulse generator 5 against continued operation or at least reduce its output power.

Finally, the possibility also exists that the comparator circuit 16 may also energise an image-forming system 20 and cause a warning symbol to be displayed on its monitor 21. As for the rest, the frame image of the kidney and of the concretion are also depicted in conventional manner on the monitor by means of a frame scanner 23, and cavitational actions are also made visible thereon if applicable.

Following the indication and recognition of cavitational actions, the focus of the sonic transducer 1 should be aligned again correctly on the concretion which is to be destroyed, which may be performed by appropriately repositioning the patient with respect to the sonic transducer. If unattenuated echoes then occur again, it is ascertained that the focus of the sonic transducer will be situated on the concretion and that the sonic transducer may be placed in operation again to generate the high-power sonic pulses.

What is claimed is:

1. In a method for predicting possible tissue damage caused by cavitation during the application of sonic high energy to the body of a patient, the sonic energy being generated extraneously by a sonic transducer and transmitted via a coupling means into the body of the patient, the sonic field traversing a spacial section internal to the body and being focused on a target zone for destruction of a target that is present within the target zone, the improvement comprising the steps of:

generating an acoustic test signal comprising at least one pulse having at least one known characteristic;

applying the acoustic test signal to the target zone;

receiving at least one reflection of the acoustic test signal from the target zone;

converting the received at least one reflection into a reception signal;

comparing the at least one known characteristic of the test signal against a corresponding characteristic of the reception signal;

using the results of said comparison as an indication of whether or not a jump in acoustic impedance is present;

generating a control signal when the results of said comparison indicate that an impedance jump is present; and using the presence or absence of the control signal as an indication of possible tissue injuries from cavitation caused by sonic high energy at the target zone.

2. A method as claimed in claim 1, wherein the reception signal is observed within a time slot, half a cycle of the reception signal being stored in a memory circuit and compared for polarity with the corresponding half-cycle of the test signal, and wherein the control signal is generated when the polarities of said half-cycles differ.

3. The method of claim 2, wherein said comparison of half-cycles is a comparison of the initial half-cycles of the reception and test signals.

4. A method as claimed in claim 1, wherein the detailed structure of said at least one reflection is analysed.

5. A method as claimed in claim 4, wherein the amplitude of at least one individual reflected half-wave is analysed by comparison with the amplitude of the test signal.

6. The method of claim 1, comprising the step of providing signaling apparatus responsive to the presence of the control signal for providing a warning signal in a form perceptible by an operator when the control signal is present.

7. The method of claim 1, comprising the steps of:

providing a controller responsive to the control signal; and providing a generator responsive to the controller, the generator providing energy to the sonic transducer at least for the generation of sonic high energy, the presence of the control signal at the controller being effective to prevent the generator from causing the transducer to generate sonic high energy.

8. The method of claim 1, comprising the steps of:

providing at least one scanner and a monitor fed by the scanner for the display of a visual monitor image;

prior to an application of sonic high energy, using the monitor and at least one scanner to locate the target zone and the target to be destroyed; and prior to the application of sonic high energy, using a monitor image to align the focus of the sonic transducer on the target.

9. The method of claim 8, comprising the step of operating the sonic transducer under reduced power to generate the acoustic test signal.

10. The method of claim 8, comprising the step of using the sonic transducer to receive the at least one reflection and processing the reflection received at the sonic transducer into the reception signal.

11. The method of claim 8, comprising the step of generating a warning on the monitor used for said locating step in response to the presence of the control signal.

12. The method of claim 1, said receiving and converting steps comprising the steps of receiving and converting at least one multiple reflection of the test signal between the target area and a transmitter of the test signal, said method comprising the steps of evaluation the wave form of the at least one multiple reflection and using the result of said evaluation as a basis of said comparison with the test signal.

13. The method of claim 1, said at least one known characteristic of the test signal being the phase of the test signal, said comparing step comprising the step of comparing the phase of the test signal to the phase of the reception signal.

14. The method of claim 1, said at least one known characteristic of the test signal being the amplitude of the test signal, said comparing step comprising the step of comparing the amplitude of the test signal to the amplitude of the reception signal.

15. Apparatus for applying sonic high energy to a target zone within the body of a patient, the apparatus comprising:

a sonic transducer capable of emitting focused high energy sound;

coupling means for coupling the focused high energy sound to the body of a patient;

a high energy pulse generator for supplying said sonic transducer with current pulses at a preset repetition rate for the production of high energy sound;

means for generating a low energy acoustic test signal of at least one pulse having at least one known characteristic;

means for applying the low energy acoustic test signal to the target zone within the body of the patient;

means for receiving at least one reflection of the acoustic test signal and converting the received reflection into an electric reception signal;

means for comparing the at least one known characteristic of the test signal against a corresponding characteristic of the reception signal to detect impedance jumps indicating possible tissue injuries from cavitation caused by sonic high energy at the target zone;

control signal generating means responsive to said comparing means for selectively generating a control signal when said comparing means detects an impedance jump; and alarm signaling means responsive to the presence of the control signal for generating a warning perceptible to a user.

16. The apparatus of claim 15, wherein said sonic transducer comprises said means for applying the low energy acoustic test signal to the target zone.

17. Apparatus for applying sonic high energy to a target zone within the body of a patient, the apparatus comprising:

a sonic transducer capable of emitting focused high energy sound;

coupling means for coupling the focused high energy sound to the body of a patient;

a high energy pulse generator for supplying said sonic transducer with current pulses at a preset repetition rate for the production of high energy sound;

means for generating a low energy acoustic test signal of at least one pulse having at least one known characteristic;

means for applying the low energy acoustic test signal to the target zone;

means for receiving at least one reflection of the acoustic test signal and converting the received reflection into an electric reception signal;

means for comparing the at least one known characteristic of the test signal against a corresponding characteristic of the reception signal to detect impedance jumps indicating possible tissue injuries from cavitation caused by sonic high energy at the target zone;

control signal generating means responsive to said comparing means for selectively generating a control signal when said comparing means detects an impedance jump, said high energy pulse generator being responsive to the presence of said control signal to suppress the generation of pulses for the production of high energy sound.

18. The apparatus of claim 17, wherein said sonic transducer comprises said means for applying the low energy acoustic test signal to the target zone.

* * * * *